US011893728B2

(12) United States Patent
Nakamura et al.

(10) Patent No.: US 11,893,728 B2
(45) Date of Patent: Feb. 6, 2024

(54) METHOD FOR DETERMINING A STATE OF A SPHERE

(71) Applicant: FUJIFILM Corporation, Tokyo (JP)

(72) Inventors: Sohichiro Nakamura, Kanagawa (JP); Ryusuke Osaki, Kanagawa (JP); Sho Onozawa, Kanagawa (JP); Akihiro Asakura, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 871 days.

(21) Appl. No.: 16/928,974

(22) Filed: Jul. 14, 2020

(65) Prior Publication Data
US 2020/0342599 A1 Oct. 29, 2020

Related U.S. Application Data

(63) Continuation of application No. PCT/JP2019/005112, filed on Feb. 13, 2019.

(30) Foreign Application Priority Data

Mar. 12, 2018 (JP) ................... 2018-044594

(51) Int. Cl.
G06T 7/00 (2017.01)
G06T 7/62 (2017.01)
(Continued)

(52) U.S. Cl.
CPC ............. G06T 7/0012 (2013.01); C12Q 1/02 (2013.01); G01N 15/06 (2013.01); G01N 21/453 (2013.01);
(Continued)

(58) Field of Classification Search
CPC .......... G06T 7/0012; G06T 7/62; C12Q 1/02; G01N 15/06; G01N 21/453; G01N 2015/0693
See application file for complete search history.

(56) References Cited

U.S. PATENT DOCUMENTS

2008/0309944 A1 12/2008 Ferraro et al.
2010/0060897 A1* 3/2010 Gustafsson ............ G02B 21/14
356/458
(Continued)

FOREIGN PATENT DOCUMENTS

JP 2009-521216 A 6/2009
JP 2015-146747 A 8/2015
(Continued)

OTHER PUBLICATIONS

European Communication pursuant to Article 94(3) EPC for corresponding European Application. No. 19766464.2, dated Mar. 29, 2023.
(Continued)

Primary Examiner — Ming Y Hon
(74) Attorney, Agent, or Firm — Birch, Stewart, Kolasch & Birch, LLP

(57) ABSTRACT

Provided is a determination method capable of non-destructively and simply determining a state of a sphere that is an aggregate of a plurality of cells. A phase difference image of a sphere that is an aggregate of a plurality of cells is generated from a hologram obtained by imaging the sphere, and a state of the sphere is determined on the basis of the phase difference image and a shape index value corresponding to a shape of the sphere.

19 Claims, 12 Drawing Sheets

(51) Int. Cl.
  *C12Q 1/02* (2006.01)
  *G01N 15/06* (2006.01)
  *G01N 21/45* (2006.01)
  *G02B 21/16* (2006.01)
  *G03H 1/04* (2006.01)

(52) U.S. Cl.
  CPC ........ *G06T 7/62* (2017.01); *G01N 2015/0693* (2013.01); *G01N 2201/0633* (2013.01); *G01N 2201/06113* (2013.01); *G02B 21/16* (2013.01); *G03H 1/0443* (2013.01); *G06T 2207/10056* (2013.01); *G06T 2207/10064* (2013.01); *G06T 2207/30024* (2013.01)

(56) References Cited

U.S. PATENT DOCUMENTS

| | | | |
|---|---|---|---|
| 2010/0328742 A1* | 12/2010 | Matsubara | G03H 1/08 359/9 |
| 2013/0088568 A1* | 4/2013 | Nolte | A61B 5/0075 348/40 |
| 2015/0219543 A1 | 8/2015 | Yamauchi et al. | |
| 2016/0011564 A1* | 1/2016 | Tanabe | G02B 26/06 359/11 |
| 2017/0261930 A1 | 9/2017 | Mathuis et al. | |
| 2017/0329281 A1 | 11/2017 | Tagawa | |
| 2017/0358081 A1* | 12/2017 | Tsumura | G01N 21/253 |
| 2018/0362917 A1* | 12/2018 | Kondo | B01D 39/20 |
| 2019/0244349 A1* | 8/2019 | Senda | G01N 15/1463 |
| 2021/0115379 A1* | 4/2021 | Inada | C12M 41/48 |
| 2021/0207120 A1* | 7/2021 | Kurakazu | C12M 23/06 |

FOREIGN PATENT DOCUMENTS

| | | |
|---|---|---|
| JP | 2015-192644 A | 11/2015 |
| JP | 2016-5437 A | 1/2016 |
| JP | 2017-163 A | 1/2017 |

OTHER PUBLICATIONS

Japanese Office Action for corresponding Japanese Application No. 2020-505699, dated Apr. 27, 2021, with English translation.
International Preliminary Report on Patentability and Written Opinion of the International Searching Authority (Forms PCT/IB/326, PCT/IB/373 and PCT/ISA/237) for International Application No. PCT/JP2019/005112, dated Sep. 24, 2020, with English translation of the Written Opinion.
International Search Report (Forms PCT/ISA/220 and PCT/ISA/210) for International Application No. PCT/JP2019/005112, dated May 7, 2019, with English translation.
Marquet et al., "Digital holographic microscopy: a noninvasive contrast imaging technique allowing quantitative visualization of living cells with subwavelength axial accuracy," Optics Letters, vol. 30, No. 5, Mar. 1, 2005, pp. 468-470.
Mihailescu et al., "Automated imaging, identification, and counting of similar cells from digital hologram reconstructions," Applied Optics, vol. 50, No. 20, Jul. 10, 2011, pp. 3589-3597.
Extended European Search Report for corresponding European Application No. 19766464.2, dated Apr. 12, 2021.
Sebesta et al., "HoloMonitor M4: holographic imaging cytometer for real-time kinetic label-free live-cell analysis of adherent cells," Progress in Biomedical Optics and Imaging, SPIE—International Society for Optical Engineering. vol. 9718. Mar. 9, 2016, pp. 971813-1-971813-10 (10 pages total).

* cited by examiner

POINT IN TIME WHERE 0 MINUTE
HAVE ELAPSED AFTER ADDING $H_2O_2$

POINT IN TIME WHERE 15 MINUTES
HAVE ELAPSED AFTER ADDING $H_2O_2$

POINT IN TIME WHERE 37 MINUTES
HAVE ELAPSED AFTER ADDING $H_2O_2$

POINT IN TIME WHERE 0 MINUTE
HAVE ELAPSED AFTER ADDING $H_2O_2$

POINT IN TIME WHERE 15 MINUTES
HAVE ELAPSED AFTER ADDING $H_2O_2$

POINT IN TIME WHERE 37 MINUTES
HAVE ELAPSED AFTER ADDING $H_2O_2$

METHOD FOR DETERMINING A STATE OF A SPHERE

CROSS-REFERENCE TO RELATED APPLICATIONS

This application is a Continuation of PCT International Application No. PCT/JP2019/005112 filed on Feb. 13, 2019, which claims priority under 35 U.S.C § 119(a) to Japanese Patent Application No. 2018-044594 filed on Mar. 12, 2018. Each of the above application(s) is hereby expressly incorporated by reference, in its entirety, into the present application.

BACKGROUND OF THE INVENTION

1. Field of the Invention

The disclosed technology relates to a determination method for determining a state of a sphere that is an aggregate of a plurality of cells.

2. Description of the Related Art

As a technique for evaluating or determining a state of a cell, for example, the following techniques are known. JP2016-005437A discloses a cell evaluation method of irradiating a cell group with illumination light, detecting transmitted light transmitted through the cell group by the irradiation of the illumination light to detect an image of the cell group, irradiating the cell group with detection light for detecting scattered light in the cell group, and evaluating the cell group on the basis of spatial spread or temporal fluctuation of intensity of the detected scattered light.

JP2017-000163A discloses a cell evaluation apparatus comprising an image input unit that inputs a first captured image obtained by imaging a cell in a neural cell differentiation process, an all-in-focus image generation unit that generates an all-in-focus image focused at a position in a thickness direction of the cell as a first original image based on at least the first captured image, a rosette extraction unit that extracts a region common to a region having a luminance distribution equal to or less than a certain level in a first original image and a region having a density difference equal to or less than a certain level in the first original image as a rosette appearing in a differentiation process, and a rosette correspondence determination unit that determines a state of the extracted rosette.

JP2015-146747A discloses a cell determination method characterized by comprising a determination step of determining the degree of differentiation of a cell on the basis of a cell thickness.

SUMMARY OF THE INVENTION

As a culture method capable of mass production of cells, a three-dimensional culture method is known in which a sphere that is an aggregate of cells are cultured in a suspended state in a medium. In the production process of cells by the three-dimensional culture, a technique for non-destructively and simply evaluating the quality of cells in the state of spheres is required from the viewpoint of easy process control. However, at the present time, a method for evaluating spheres having various sizes randomly present in a three-dimensional space has not been established, and in particular, it is difficult to directly observe a density and survival situation of cells inside the sphere. For this reason, evaluation is performed by applying a conventional two-dimensional culture method, but as the number of cells to be cultured increases, the number of evaluation steps increases, and thus much manpower and much time are required. In the evaluation to which the conventional two-dimensional culture method is applied, a treatment involving cell destruction such as decomposing the sphere into a single cell or adding a fluorescent coloring agent is required.

An object of the disclosed technology is to determine a state of a sphere that is an aggregate of a plurality of cells, in a non-destructive and simple manner.

A determination method according to the disclosed technology includes generating a phase difference image of a sphere that is an aggregate of a plurality of cells from a hologram obtained by imaging the sphere; and determining a state of the sphere on the basis of the phase difference image and a shape index value corresponding to a shape of the sphere.

In the determination method according to the disclosed technology, it is possible to determine the state of the sphere in a non-destructive and simple manner.

In the determination method according to the disclosed technology, a determination regarding at least one of a survival rate, a density, a homogeneity, or an undifferentiated state deviation of the plurality of cells included in the sphere, or an outer shape of the sphere may be performed on the basis of the phase difference image and the shape index value.

In the determination method according to the disclosed technology, a total phase difference amount that is a value obtained by integrating a phase difference amount of each of a plurality of pixels constituting the phase difference image may be derived; and the state of the sphere may be determined using a correlation between the total phase difference amount and the shape index value.

In the determination method according to the disclosed technology, a reference correlation trend line indicating a reference for the correlation between the total phase difference amount and the shape index value may be compared with a correlation between a total phase difference amount and a shape index value for a sphere to be determined; and the state of the sphere to be determined may be determined according to a degree of deviation of the correlation between the total phase difference amount and the shape index value for the sphere to be determined from the reference correlation trend line. For example, in a case where a width of the deviation of the correlation between the total phase difference amount and the shape index value for the sphere to be determined from the reference correlation trend line exceeds a threshold value, it may be determined that there is an abnormality in at least one of a survival rate, a density, or a homogeneity of cells included in the sphere to be determined, or an outer shape of the sphere.

In the determination method according to the disclosed technology, a reference correlation trend line indicating a reference for the correlation between the total phase difference amount and the shape index value may be compared with a correlation between a total phase difference amount and a shape index value for each of a plurality of spheres belonging to a culture lot to be determined; and a quality of the culture lot to be determined may be determined according to at least one of a state of deviation or a degree of deviation of the correlation between the total phase difference amount and the shape index value for the culture lot to be determined from the reference correlation trend line.

In the determination method according to the disclosed technology, the shape index value may be any one of a volume, a cross-sectional area, a particle diameter, or a circumferential length of the sphere.

In the determination method according to the disclosed technology, a phase difference amount density may be derived by dividing a total phase difference amount by a volume of the sphere, the a total phase difference amount is a value obtained by integrating a phase difference amount of each of a plurality of pixels constituting the phase difference image; and the state of the sphere may be determined on the basis of the phase difference amount density.

In the determination method according to the disclosed technology, it is preferable that the phase difference image used for the determination of the state of the sphere is a phase difference image in which variation in a phase difference amount between a plurality of pixels constituting the phase difference image is the maximum among a plurality of phase difference images that are generable from the hologram.

According to the disclosed technology, a state of a sphere that is an aggregate of a plurality of cells can be determined in a non-destructive and simple manner.

DESCRIPTION OF THE PREFERRED EMBODIMENTS

Figure 1:
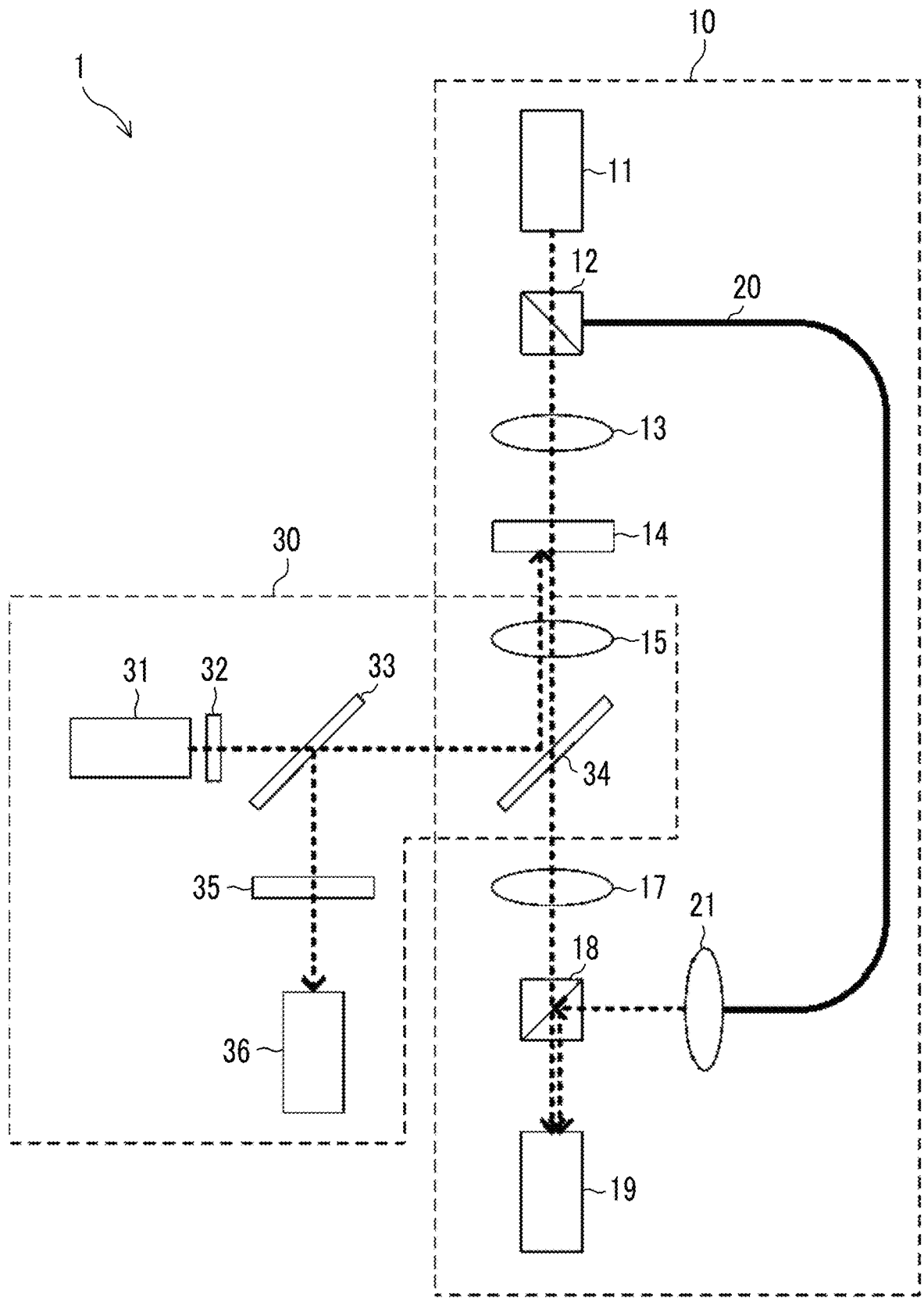
FIG. 1 is a diagram showing an example of a configuration of an imaging system used for performing a determination method according to an embodiment of the disclosed technology.

Hereinafter, embodiments of the present invention will be described with reference to the drawings. In the drawings, substantially the same or equivalent components or portions are denoted by the same reference numerals.

A determination method according to the embodiments of the disclosed technology includes generating a phase difference image of a sphere that is an aggregate of a plurality of cells from a hologram obtained by imaging the sphere, and determining a state of the sphere on the basis of the phase difference image and a shape index value corresponding to a shape of the sphere.

FIG. 1 is a diagram showing an example of a configuration of an imaging system 1 used for performing a determination method according to an embodiment of the disclosed technology. The imaging system 1 is configured to include a hologram optical system 10 for acquiring a hologram of a sphere using a known digital holography technique, and a fluorescence microscope optical system 30 for performing fluorescence microscope observation of the sphere.

The digital holography technique is a technique in which an image generated by interference between object light transmitted through or reflected by an object and reference light coherent with the object light is imaged using an image sensor, and numerical calculation based on light propagation is performed on the image obtained by the imaging, thereby restoring a wavefront of a light wave from the object. According to the digital holography technique, it is possible to quantify a phase distribution of the object and acquire three-dimensional information of the object without mechanically moving a focal position.

The hologram optical system 10 is configured to include a laser light source 11, beam splitters 12 and 18, collimating lenses 13 and 21, an objective lens 15, an imaging lens 17, and a complementary metal oxide semiconductor (CMOS)

camera 19. A sphere as a sample 14 set on a sample stage is disposed between the collimating lens 13 and the objective lens 15.

As the laser light source 11, for example, a HeNe laser having a wavelength of 632.8 nm can be used. Laser light emitted from the laser light source 11 is split into two laser lights by the beam splitter 12. One of the two laser lights is object light and the other is reference light. The object light is collimated by the collimating lens 13, and then irradiated onto a sphere as the sample 14 set on the sample stage. An image formed by the object light transmitted through the sphere is magnified by the objective lens 15. The object light transmitted through the objective lens 15 is collimated again by the imaging lens 17, and then is formed on an imaging surface of a CMOS camera 19 via the beam splitter 18. On the other hand, the reference light is guided to the front of the collimating lens 21 by the optical fiber 20. The reference light emitted from the optical fiber 20 is collimated by the collimating lens 21 and is incident on the imaging surface of the CMOS camera 19 via the beam splitter 18. The hologram generated by the interference between the object light and the reference light is recorded by the CMOS camera 19. An off-axial optical system in which optical axis directions of the object light and the reference light incident on the imaging surface of the CMOS camera 19 are different from each other may be configured.

On the other hand, the fluorescence microscope optical system 30 includes an excitation light source 31, an excitation filter 32, an ON/OFF switching mirror 33, a dichroic mirror 34, an objective lens 15, a spectral filter 35, and a CMOS camera 36.

A mercury lamp, for example, can be used as the excitation light source 31. The excitation filter 32 transmits light in a wavelength range of, for example, 450 nm to 490 nm among excitation lights emitted from the excitation light source 31. The excitation light transmitted through the excitation filter 32 is irradiated onto the sphere that is the sample 14 set on the sample stage, via the ON/OFF switching mirror 33, the dichroic mirror 34, and the objective lens 15. In a case where a fluorescent coloring agent added to the sphere is irradiated with excitation light, fluorescence emitted from the fluorescent coloring agent is incident on the imaging surface of the CMOS camera 36 via the objective lens 15, the dichroic mirror 34, the ON/OFF switching mirror 33, and the spectral filter 35. The spectral filter 35 transmits, for example, light in a wavelength range of 515 nm or more among the fluorescence emitted from the fluorescent coloring agent.

According to the imaging system 1 according to the present embodiment, it is possible to perform hologram observation by the hologram optical system 10 and fluorescence microscopic observation by the fluorescence microscope optical system 30 in parallel. The configuration of the above-described imaging system 1 is merely an example, and the present invention is not limited to the above-described configuration. Any imaging system capable of acquiring a hologram using digital hologram technology can be used to perform the determination method according to the disclosed technology.

Hereinafter, an example of a method of acquiring a phase difference image of a sphere from a hologram of the sphere acquired by using the imaging system 1 will be described.

Figure 2A:
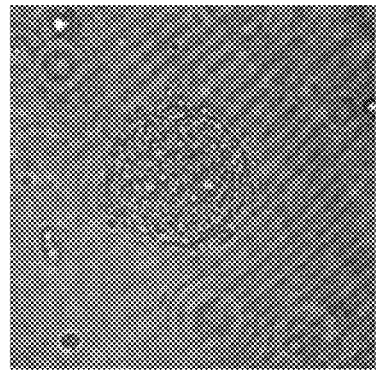
FIG. 2A is a diagram showing an example of a hologram used for performing a determination method according to an embodiment of the disclosed technology.
Figure 2B:
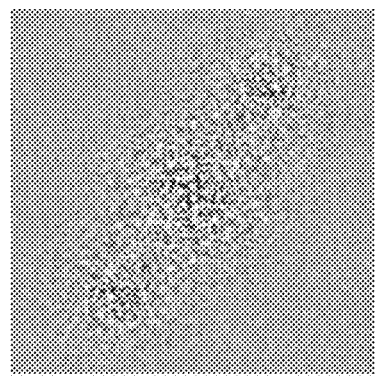
FIG. 2B is a diagram showing an example of a Fourier transform image of a sphere.

First, the hologram exemplified in FIG. 2A acquired by the CMOS camera 19 is subjected to a two-dimensional Fourier transform to extract a complex amplitude component of only the object light. FIG. 2B is an example of a Fourier transform image of the sphere obtained by this processing.

Figure 2C:
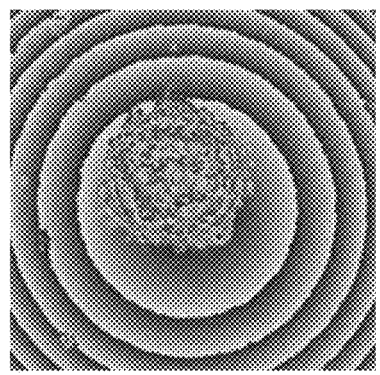
FIG. 2C is a diagram showing an example of a phase difference image of a sphere before unwrapping.
Figure 2D:
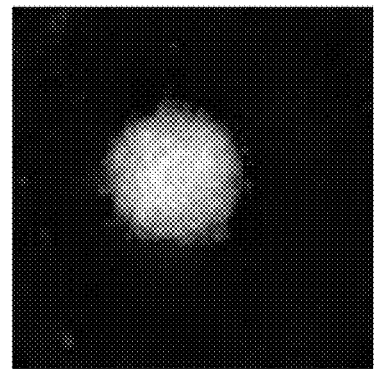
FIG. 2D is a diagram showing an example of a phase difference image of a sphere after unwrapping.

Next, for example, the angular spectrum method is applied to restore the image showing the phase of the sphere at an arbitrary spatial position. FIG. 2C is an example of a phase difference image before unwrapping of the sphere obtained by this processing. The phase of the sphere at this point is convolved with a value of 0 to $2\pi$. Therefore, for example, by applying a phase connection (unwrapping) method such as unweighted least squares or Flynn's algorithm to join portions of $2\pi$ or more, a final phase difference image of the sphere as exemplified in FIG. 2D can be obtained. Many unwrapping methods have been proposed, and an appropriate method that does not cause phase mismatch may be appropriately selected.

Figure 3:
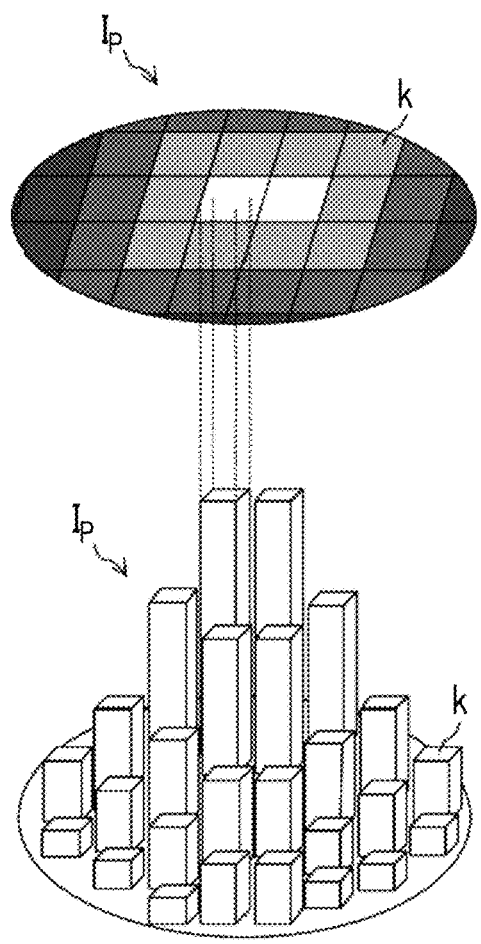
FIG. 3 is a diagram showing the concept of a phase difference image according to an embodiment of the disclosed technology.

FIG. 3 is a diagram showing the concept of a phase difference image $I_P$. In the lower part of FIG. 3, a phase difference amount at each pixel k of the phase difference image $I_P$ is three-dimensionally displayed. In the upper part of FIG. 3, the phase difference amount at each pixel k of the phase difference image $I_P$ is shown on a plane in gray scale.

Here, a phase difference amount $\theta$ in the phase difference image $I_P$ is represented by Formula 1 in a case where $\theta_B$ is a phase of a background (region where the sphere does not exist) existing in the same focal plane of the phase difference image $I_P$, and $\theta_S$ is a phase of a region where the sphere exists. In addition, the term "phase" in the present specification is a phase of an electric field amplitude in a case where light is regarded as an electromagnetic wave, and is used in a more general sense.

$$\theta = \theta_S - \theta_B \quad (1)$$

In addition, a phase difference amount $\theta_k$ at each pixel k of the phase difference image $I_P$ can be represented by Formula 2. Here, $n_k$ is refractive index of the sphere at the portion corresponding to each pixel k of the phase difference image $I_P$, $d_k$ is a thickness of the sphere at the portion corresponding to each pixel k of the phase difference image $I_P$, and $\lambda$ is a wavelength of the object light in the hologram optical system 10.

$$\theta_k = 2\pi \frac{n_k - d_k}{\lambda} \quad (2)$$

The phase difference image of the sphere is an image showing an optical path length distribution of the object light transmitted through the sphere. Since the optical path length in the sphere corresponds to the product of the refractive index of the sphere and the thickness of the sphere, the phase difference image of the sphere includes information on the refractive index and the thickness (shape) of the sphere, as also shown in Formula 2.

Accurate information matching the actual condition of the sphere cannot be obtained from the phase difference image that is out of focus with respect to the sphere by the influence of the spread due to diffraction. Therefore, it is preferable to focus on the sphere in a case of acquiring the phase difference image from the hologram acquired by the CMOS camera 19. Here, "focusing on a sphere" means obtaining a phase difference image sliced near a center of a spherical sphere. A more accurate determination result can be obtained by determining the state of the sphere using the phase difference image focused on the sphere. A user may determine the state of the sphere on the basis of the acquired phase difference image of the sphere. Alternatively, a computer that has learned a determination condition may determine the state of the sphere on the basis of the acquired phase difference image of the sphere.

It is preferable to automate the focusing of the phase difference image without manual operation. By automating the focusing, it is possible to eliminate the arbitrariness by an operator and further shorten the processing time. The inventors have found an automatable focusing technique described below.

Figure 4:
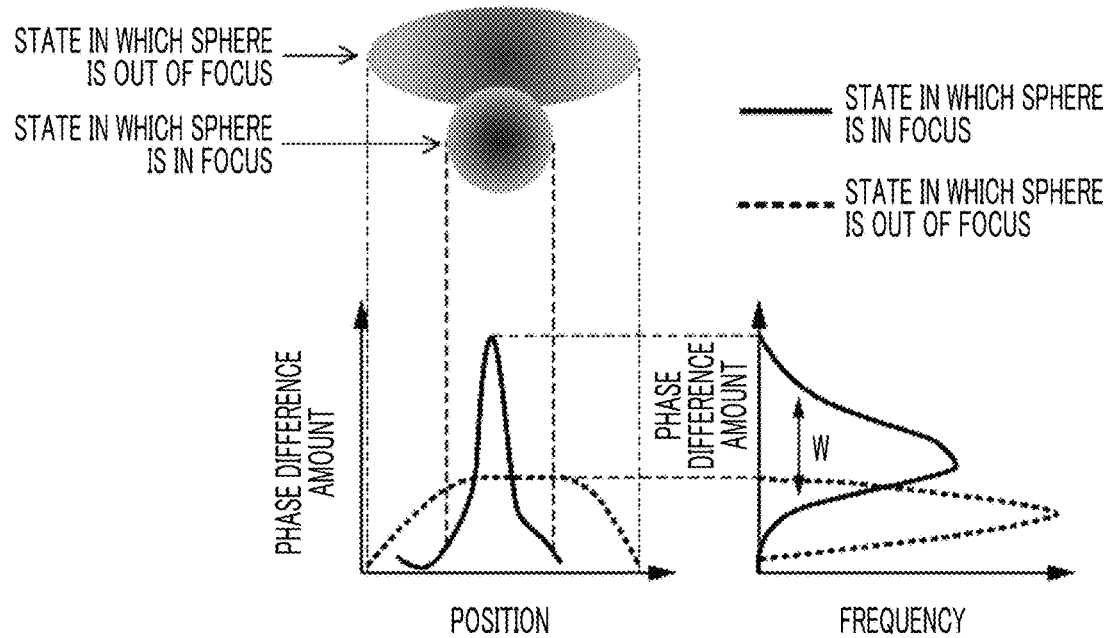
FIG. 4 is an explanatory diagram related to focusing of a phase difference image according to an embodiment of the disclosed technology.

The graph on the left side of FIG. 4 is a graph showing an example of a relationship between the position of the sphere in the plane direction and the phase difference amount in the phase difference image, in which a solid line corresponds to a state in which the sphere is in focus and a dotted line corresponds to a state in which the sphere is out of focus. In a case where the sphere is in focus, a steep peak appears at a specific position in the phase difference image. On the other hand, in a case where the sphere is out of focus, the peak is lower and smoother than the case where the sphere is in focus.

The graph on the right side of FIG. 4 is an example of a histogram of the phase difference amount in the phase difference image of the sphere, in which a solid line corresponds to a state in which the sphere is in focus and a dotted line corresponds to a state in which the sphere is out of focus. In the case where the sphere is in focus, a width w of a curve (variation in the phase difference amount) is relatively large, and in the case where the sphere is out of focus, the width w of the curve (variation in the phase difference amount) is relatively small.

Therefore, focusing can be realized by acquiring phase difference image of the sphere for each of different focal positions (slice positions), obtaining the width w of the curve in the histogram of the phase difference amount (variation in the phase difference amount) for each of the acquired phase difference image, and extracting the phase difference image having the maximum width w among the obtained widths w as the phase difference image focused on the sphere.

Figure 5:
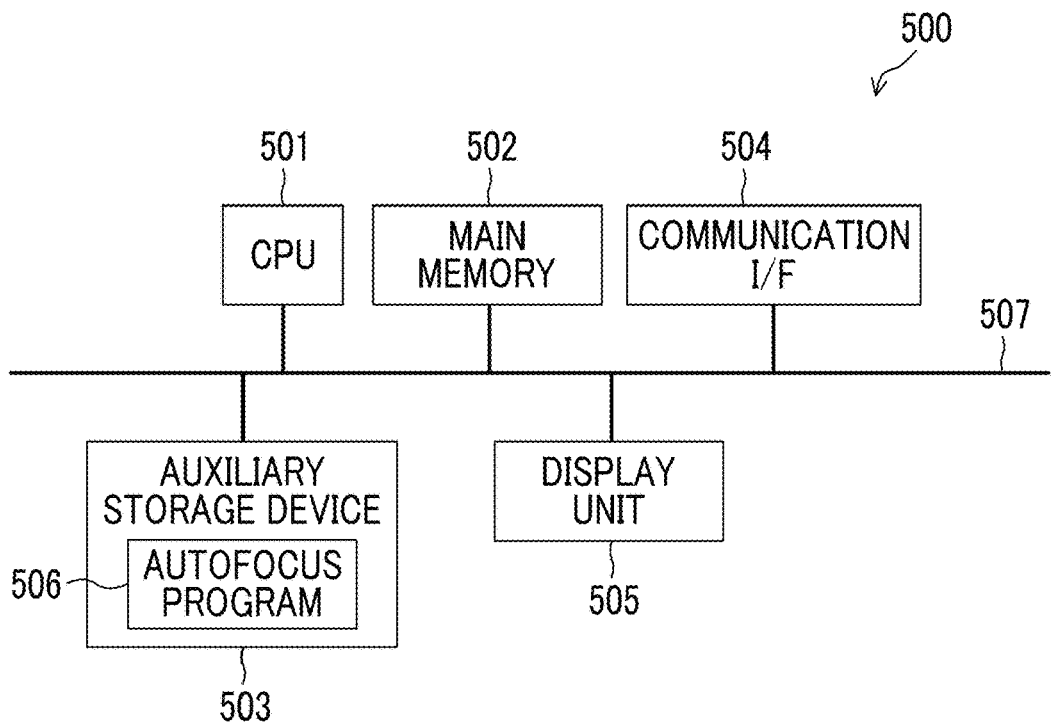
FIG. 5 is an example of a hardware configuration of a computer that performs autofocus processing according to an embodiment of the disclosed technology.

The above-described focusing can be automated using a computer. FIG. 5 is an example of a hardware configuration of a computer 500 that performs an autofocus processing for automatically performing the above-described focusing.

The computer 500 includes a central processing unit (CPU) 501, a main memory 502 as a temporary storage region, a nonvolatile auxiliary storage device 503, a communication interface (I/F) 504 for communicating with the CMOS camera 19, and a display unit 505 such as a liquid crystal display. The CPU 501, the main memory 502, the auxiliary storage device 503, the communication I/F 504, and the display unit 505 are each connected to a bus 507. The auxiliary storage device 503 houses an autofocus program 506 which describes the procedure of the above-described autofocus processing. In the computer 500, the CPU 501 executes the autofocus program 506 to perform the autofocus processing.

Figure 6:
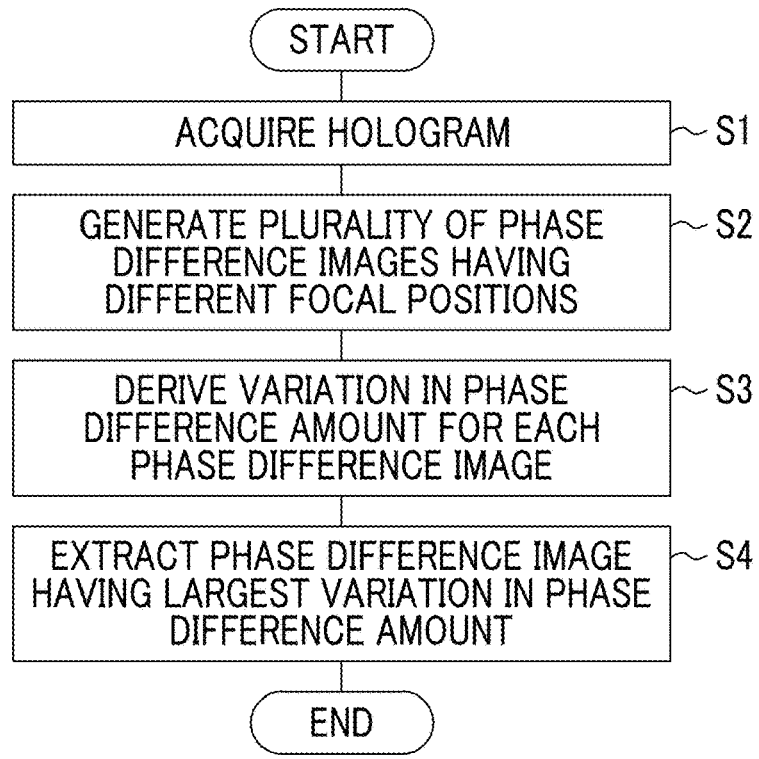
FIG. 6 is a flowchart showing an example of a flow of an autofocus processing according to an embodiment of the disclosed technology.

FIG. 6 is a flowchart showing an example of a flow of the autofocus processing performed by the computer 500.

In step S1, the CPU 501 acquires a hologram of the sphere from the CMOS camera 19.

In step S2, the CPU 501 generates a plurality of phase difference images having different focal positions (slice positions) from the acquired hologram.

In step S3, the CPU 501 derives the variation in the phase difference amount for each phase difference image for each focal position (slice position). The CPU 501 may derive, for example, a difference between the maximum value and the minimum value of the phase difference amount in the phase difference image as the variation of the phase difference amount in the phase difference image.

In step S4, the CPU 501 extracts a phase difference image having the largest variation in the phase difference amount derived in step S3 as the phase difference image focused on the sphere among the plurality of phase difference images having different focal positions (slice positions).

Figure 7:
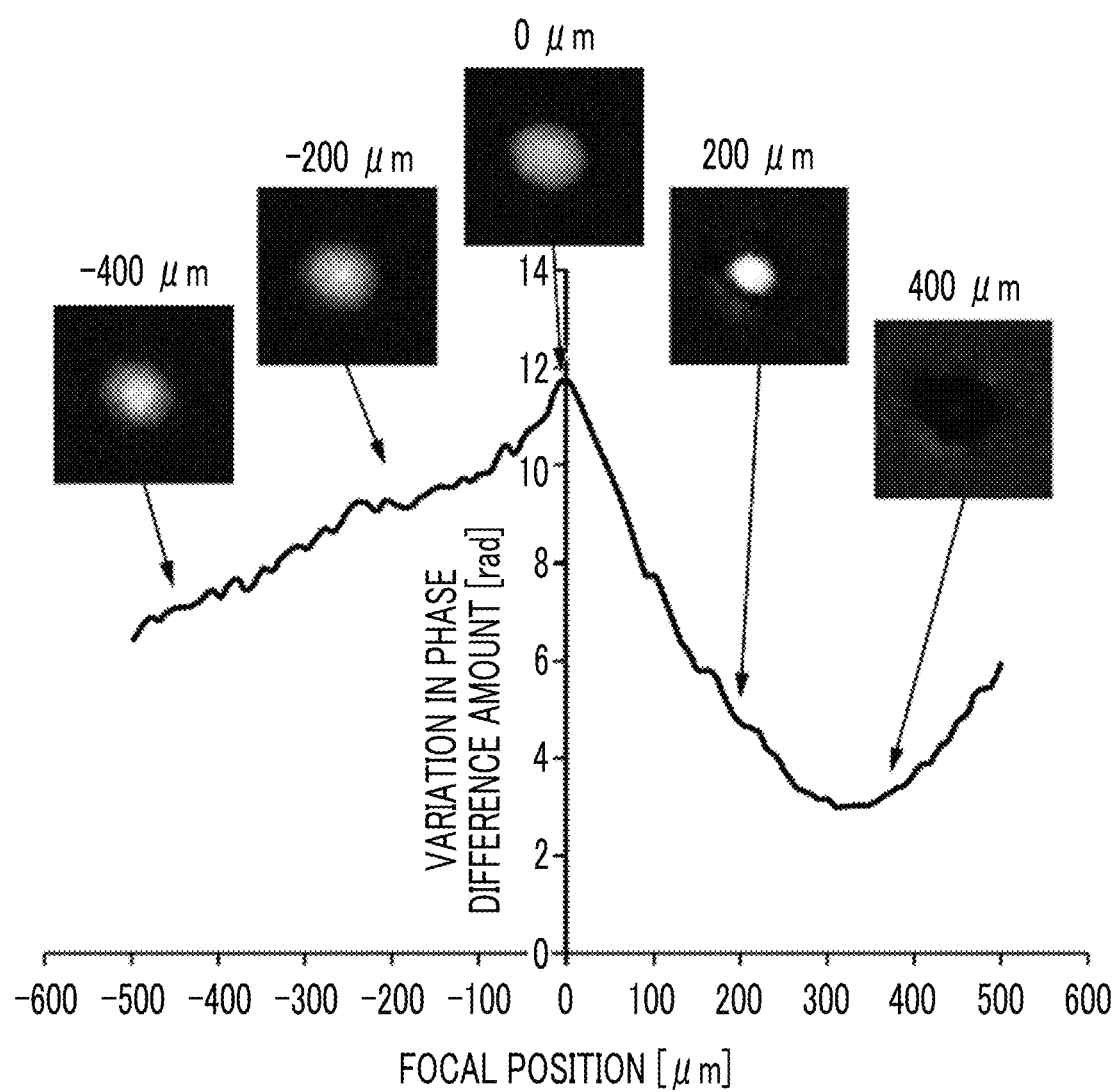
FIG. 7 is a graph showing an example of a relationship between a focal position and variation in a phase difference amount in a phase difference image of a sphere according to an embodiment of the disclosed technology.

FIG. 7 is a graph showing an example of the relationship between the focal position (slice position) and the variation in the phase difference amount in the phase difference image of the sphere. FIG. 7 exemplifies phase difference images and graphs of spheres corresponding to focal positions of −400 μm, −200 μm, 0 μm, +200 μm, and +400 μm. In FIG. 7, a focal position in which the variation in the phase difference amount is the maximum is set to 0 μm. According to the above-described autofocus processing, the phase difference image corresponding to the focal position 0 μm in which the variation in the phase difference amount is the maximum is extracted as the focused phase difference image. In the phase difference image corresponding to the focal position 0 μm in which the variation of the phase difference amount is maximum, a contour of the sphere becomes the clearest.

The determination method according to an embodiment of the disclosed technology includes determining the state of the sphere on the basis of a phase difference image of the sphere and a shape index value of the sphere. That is, the state of the sphere is determined by analyzing the phase difference image of the sphere in association with the shape index value of the sphere. The state of the sphere to be determined includes, for example, a survival rate, a density, a homogeneity, or an undifferentiated state deviation of a plurality of cells included in the sphere, or an outer shape of the sphere.

As the shape index value of the sphere, for example, a volume of the sphere, a cross-sectional area, a particle diameter, a circumferential length, or the like can be used. The particle diameter and circumferential length of the sphere can be obtained directly from the image of the sphere in the phase difference image focused on the sphere (that is, the phase difference image sliced near the center of the sphere). The cross-sectional area of the sphere can be derived, for example, as a cross-sectional area of a circle whose diameter is the particle diameter of the sphere. The volume of the sphere can be derived as, for example, the volume of a sphere having a diameter of the particle diameter of the sphere.

The determination method according to the embodiment of the disclosed technology may include deriving a total phase difference amount $\theta_A$ that is a value obtained by integrating a phase difference amount of each of a plurality of pixels constituting the phase difference image, and determining the state of the sphere using a correlation between the total phase difference amount $\theta_A$ and the shape index value.

The total phase difference amount $\theta_A$ is represented by Formula 3. However, s is the area of each pixel k of the phase difference image, and $v_k$ is the volume of the sphere in the portion corresponding to each pixel k of the phase difference image. As shown in Formula 3, the total phase difference amount $\theta_A$ corresponds to a value obtained by integrating the phase difference amount $\theta_k$ for each pixel of the phase difference image of the sphere for all pixels k. In Formula 3, $d_k$ shows a thickness of the sphere portion projected on the pixel k, and $n_k$ represents a difference in refractive index between a background culture solution and the inside of the sphere.

In Formula 3, $v_k = d_k \cdot s$ is used.

Here, according to Formula 3, the unit of the total phase difference amount $\theta_A$ is the scale of the area, for example, [μm²], but in a case where a comparison is not performed between the image sensors, the unit of the total phase difference amount $\theta_A$ may be simply set to [pixel] as the sum of the phase difference amount $\theta_k$ for each pixel per 1 pixel, that is, s=1 [pixel].

$$\theta_A = \sum_{k=1}^{N} \theta_k \cdot s = \frac{2\pi}{\lambda} \sum_{k=1}^{N} n_k \cdot d_k \cdot s = \frac{2\pi}{\lambda} \sum_{k=1}^{N} n_k \cdot r_k \quad (3)$$

The determination method according to the embodiment of the disclosed technology may include comparing a reference correlation trend line indicating a reference for the correlation between the total phase difference amount $\theta_A$ and the shape index value of the sphere with a correlation between the total phase difference amount $\theta_A$ and the shape index value for a sphere to be determined, and determining the state of the sphere to be determined according to a degree of deviation of the correlation for the sphere to be determined from the reference correlation trend line. In this case, in a case where a width of the deviation of the correlation for the sphere to be determined from the reference correlation trend line exceeds a threshold value, it may be determined that there is an abnormality in at least one of a survival rate, a density, or a homogeneity of cells included in the sphere to be determined, or an outer shape of the sphere.

For example, the state of the sphere to be determined may be determined according to the degree of deviation from the reference correlation trend line of a plot of the sphere to be determined which is plotted on a graph in which the total phase difference amount $\theta_A$ is taken on one axis and the shape index value is taken on the other axis. In this case, in a case where a width of a deviation of the above-described plot from the reference correlation trend line exceeds a threshold value, it may be determined that there is an abnormality in at least one of a survival rate, a density, or a homogeneity of cells included in the sphere to be determined, or an outer shape of the sphere.

The determination method according to the embodiment of the disclosed technology can include comparing the reference correlation trend line with the correlation between the total phase difference amount $\theta_A$ and the shape index value for each of the plurality of spheres belonging to a culture lot to be determined, and determining a quality of the culture lot to be determined according to at least one of the state of deviation or the degree of deviation of the correlation for the culture lot to be determined from the reference correlation trend line.

For example, the quality of the culture lot may be determined according to at least one of the state of deviation or the degree of deviation from the reference correlation trend line of the plot for each of the plurality of spheres belonging to the culture lot to be determined which is plotted on a graph in which the total phase difference amount $\theta_A$ is taken on one axis and the shape index value is taken on the other axis.

For example, it is possible to use, as the reference correlation trend line, a correlation line between the total phase difference amount $\theta_A$ and the shape index value of the sphere, which is acquired in advance for a healthy sphere (standard sample). In addition, a regression line derived from each plot of the sphere to be determined using, for example, the least squares method may be used as the reference correlation trend line.

The determination method according to the embodiment of the disclosed technology may include deriving a phase difference amount density $D_P$ by dividing the total phase difference amount $\theta_A$ by the volume of the sphere, and determining the state of the sphere on the basis of the derived phase difference amount density $D_P$.

The phase difference amount density $D_P$ is represented by Formula 4. However, V is the volume of the sphere. As shown in Formula 4, the phase difference amount density $D_P$ corresponds to a value obtained by dividing the total phase difference amount $\theta_A$ by a volume V of the sphere. Healthy cells are considered to maintain a constant internal refractive index different from the refractive index of the medium due to their homeostasis. On the other hand, it is considered that dead cells lose homeostasis and the internal refractive index becomes almost the same as that of the medium. Therefore, it is considered possible to use the phase difference amount density $D_P$ as an index indicating the state of cells. For example, it can be determined that the state of the sphere is good in a case where the phase difference amount density $D_P$ acquired for the sphere to be determined is equal to or more than a threshold value, and it can be determined that the state of the sphere is abnormal in a case where the phase difference amount density $D_P$ is less than the threshold value. Since $2\pi/\lambda$ can be treated as a constant, the multiplication of a $2\pi/\lambda$ may be omitted in a case of deriving the phase difference amount density $D_P$. Here, in a case where the volume average refractive index difference $N_{ave}$ of the sphere is $N_{ave} = \Sigma nk \cdot (v_k/V)$, since the Formula 4 is $D_P = (2\pi/\lambda) \times N_{ave}$, the phase difference density is a value obtained by normalizing the volume-averaged difference in refractive index of sphere by the length of wavelength. In the present specification, V is obtained by calculating a sphere equivalent diameter from the cross-sectional image of the phase image of the sphere. A more accurate ellipsoidal sphere is also possible.

$$D_P = \frac{\theta_A}{V} = \frac{2\pi}{\lambda} \sum_{k=1}^{N} n_k \cdot \frac{v_k}{V} \quad (4)$$

An example of the determination method according to the disclosed technology will be described below.

Example 1

A sphere of an induced pluripotent stem (iPS) cell cultured by the three-dimensional culture method is set on the sample stage of the imaging system 1 shown in FIG. 1, and holograms of the plurality of spheres are captured by the CMOS camera 19. A computer numerical calculation is performed on the acquired hologram of each sphere to acquire the phase difference image sliced near the center of the sphere.

Figure 8:
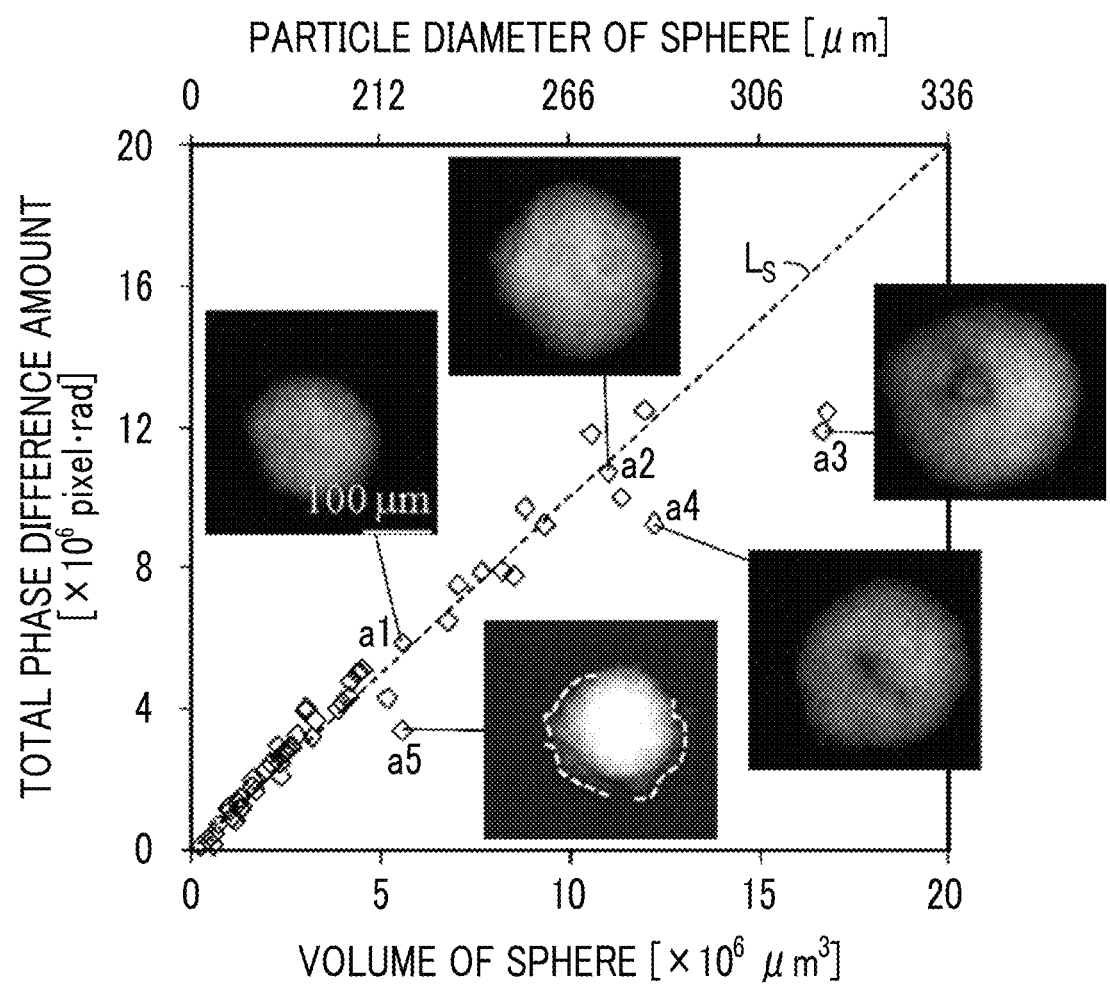
FIG. 8 is a graph showing an example of correlation properties between a volume of a sphere and a total phase difference amount according to an embodiment of the disclosed technology.

From the obtained phase difference image of each sphere, the volume is derived as the shape index value of each sphere. Further, for the phase difference image of each sphere, the total phase difference amount $\theta_A$ shown by Formula 3 is derived. Correlation properties between the volume of the sphere and the total phase difference amount $\theta_A$ are acquired by forming a plot for each sphere on a graph in which the volume of the sphere is taken on the lateral axis and the total phase difference amount $\theta_A$ is taken on the vertical axis. FIG. 8 is a graph showing the correlation properties between the volume of the sphere and the total phase difference amount $\theta_A$. As shown in FIG. 8, it is confirmed that the total phase difference amount $\theta_A$ and the volume of the sphere have a proportional relationship. FIG. 8 shows a reference correlation trend line $L_S$ and a plot showing a reference for correlation between the volume of the sphere and the total phase difference amount $\theta_A$. A regression line derived from each plot shown in FIG. 8 is applied as the reference correlation trend line $L_S$.

FIG. 8 shows phase difference images of spheres corresponding to plots a1 and a2 existing on the reference correlation trend line $L_S$, and phase difference images of spheres corresponding to plots a3, a4, and a5 existing at a position deviated from the reference correlation trend line $L_S$. For the spheres corresponding to the plots a1 and a2 existing on the reference correlation trend line $L_S$, a phase difference image having uniform luminance over the entire sphere is obtained. This indicates that the plurality of cells constituting the sphere are homogeneous, the density of the cells in the sphere is uniform, and the like. On the other hand, for the spheres corresponding to the plots a3 and a4 existing at the positions deviated from the reference correlation trend line $L_S$, a phase difference image in which the luminance of the central portion is lower than that of other portions is obtained. This indicates that the plurality of cells constituting the sphere are an inhomogeneity, the density of the cells in the sphere is non-uniform, and the like. In addition, for the sphere corresponding to the plot a5 existing at the position deviated from the reference correlation trend line $L_S$, a phase difference image in which the unevenness of a contour line of the sphere is remarkable is obtained. This indicates that an abnormality occurs in the cells constituting the sphere.

From the above results, it can be said that the state of the sphere can be determined by using a correlation between the total phase difference amount $\theta_A$ and the volume, which is an example of the shape index value of the sphere. In addition, it can be said that the reference correlation trend line $L_S$ indicating the correlation between the total phase difference amount $\theta_A$ and the volume of the sphere can be compared with a correlation between the total phase difference amount $\theta_A$ and the shape index value for a sphere to be determined, and the state of the sphere can be determined according to a degree of deviation of the correlation for the sphere to be determined from the reference correlation trend line $L_S$. Specifically, it can be said that the state of each sphere can be determined according to the degree of deviation from the reference correlation trend line $L_S$ of the plot of the sphere to be determined which is plotted on the graph in which the volume of the sphere is taken on one axis and the total phase difference amount $\theta_A$ is taken on the other axis. Therefore, for example, for spheres in which a minus width of the total phase difference amount $\theta_A$ from the reference correlation trend line $L_S$ is equal to or more than a threshold value, it can be determined that there is an abnormality in at least one of the density or homogeneity of the plurality of cells included in the sphere, or an outer shape of the sphere.

Although the volume of the sphere is used as the shape index value of the sphere in this example, it is also possible to use the cross-sectional area, particle diameter, or circumferential length of the sphere instead of this. Even in a case where any of these shape index values is used, it is possible to determine the state of the sphere by using the correlation with the total phase difference amount $\theta_A$.

Example 2

In this example, a culture lot including a plurality of spheres is used as an object to be determined. The culture lot to be determined are a good lot and a bad lot shown in Table 1 below. The sphere belonging to the good lot and the sphere belonging to the bad lot are spheres of iPS cells cultured by the three-dimensional culture method, respectively. A proliferation rate of cells from the first day to the fifth day of a culture period is 20 times in the sphere belonging to the good lot and 3.7 times in the sphere belonging to the bad lot. The survival rate of cells on the fifth day of culture is 90.2% in the sphere belonging to the good lot and 64.1% in the sphere belonging to the bad lot.

TABLE 1

|  | Proliferation rate | Survival rate |
| --- | --- | --- |
| Good lot | 20.0 times | 90.2% |
| Bad lot | 3.7 times | 64.1% |

For each of the good lot and the bad lot, the sphere as the sample 14 is set on the sample stage of the imaging system 1 shown in FIG. 1, and holograms of the plurality of spheres are imaged by the CMOS camera 19. A computer numerical calculation is performed on the acquired hologram of each sphere to acquire the phase difference image sliced near the center of the sphere.

Figure 9A:
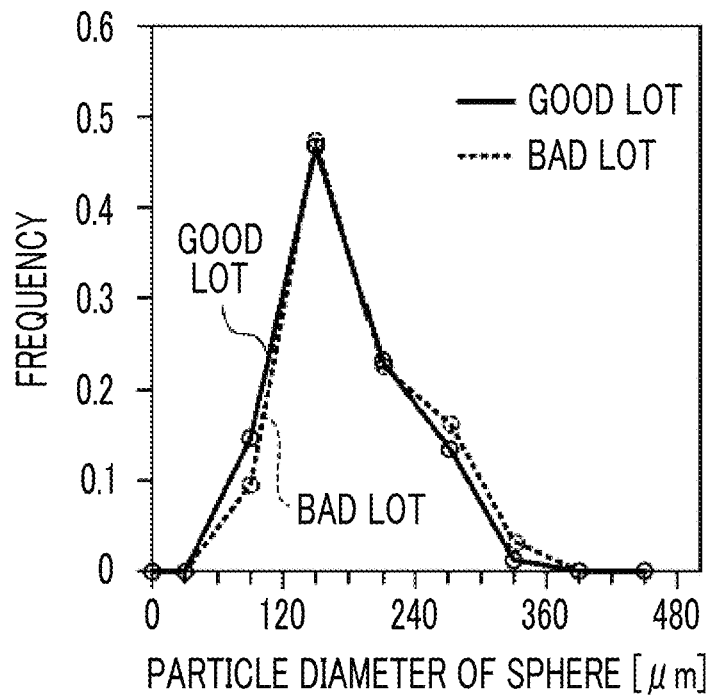
FIG. 9A is a histogram of a particle diameter of a sphere derived for each of a good lot and a bad lot according to an embodiment of the disclosed technology.

The particle diameter of each sphere is derived from the obtained phase difference image of each sphere, and a histogram of the particle diameter of the sphere is acquired. FIG. 9A is the histogram of the particle diameter of the sphere derived for each of the good lot and the bad lot. As shown in FIG. 9A, there is no significant difference in the histogram between the good lot and the bad lot. This indicates that the state of the sphere is difficult to be reflected in the particle diameter of the sphere, and it is difficult to determine the state of the sphere on the basis of only the particle diameter of the sphere.

Figure 9B:
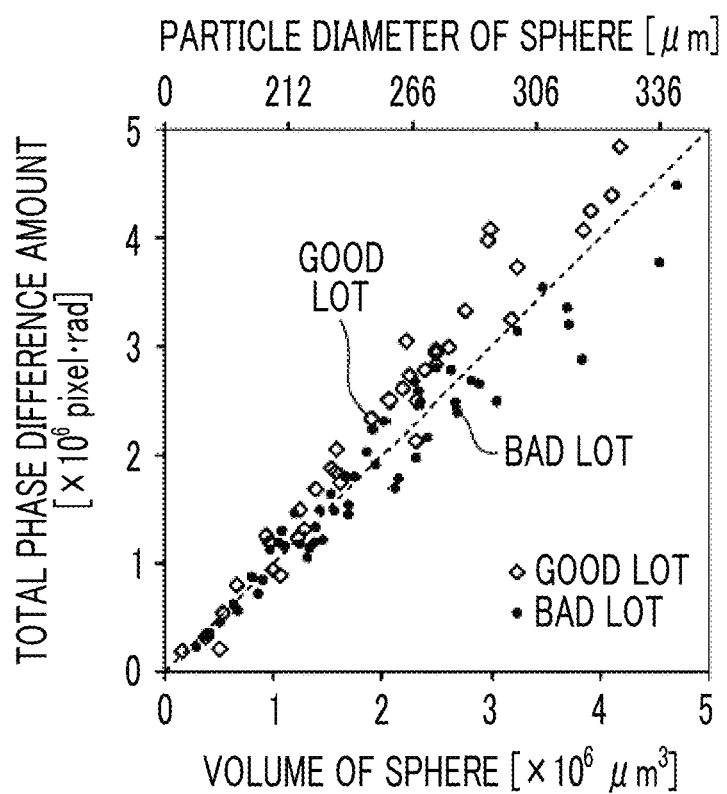
FIG. 9B is a graph showing an example of correlation properties between a volume of a sphere and a total phase difference amount acquired for each of a good lot and a bad lot according to the embodiment of the disclosed technology.

Next, the volume is derived as the shape index value of each sphere from the phase difference image of each sphere obtained for each of the good lot and the bad lot, and the total phase difference amount $\theta_A$ shown by Formula 3 is derived for the phase difference image of each sphere. The correlation properties between the volume of the sphere and the total phase difference amount $\theta_A$ are acquired by forming the plot for each sphere of each culture lot on the graph in which the volume of the sphere is taken on the lateral axis and the total phase difference amount $\theta_A$ is taken on the vertical axis. FIG. 9B is a graph showing an example of the correlation properties between the volume of the sphere and the total phase difference amount $\theta_A$ acquired for each of the good lot and the bad lot. FIG. 9B shows the reference correlation trend line $L_S$ and the plot. As shown in FIG. 9B, in the good lot, the number of spheres in which the total phase difference amount $\theta_A$ falls below the reference correlation trend line $L_S$ is small, whereas in the bad lot, the number of spheres in which the total phase difference amount $\theta_A$ falls below the reference correlation trend line $L_S$ is larger than that in the good lot.

From the above results, it can be said that the quality of the culture lot can be determined by using a correlation between the total phase difference amount $\theta_A$ and the volume, which is an example of the shape index value of the sphere. In addition, it can be said that the reference correlation trend line $L_S$ indicating the correlation between the total phase difference amount $\theta_A$ and the volume of the sphere can be compared with the correlation for the sphere belonging to the culture lot to be determined, and the quality of the culture lot can be determined according to the degree of deviation of the correlation for the culture lot to be determined from the reference correlation trend line $L_S$. Specifically, it can be said that the state of the culture lot can be determined on the basis of at least one of the state of deviation (whether or not the plot falls below the reference correlation trend line $L_S$) or the degree of deviation from the reference correlation trend line $L_S$ of the plot of each sphere belonging to the culture lot to be determined which is plotted on the graph in which the volume of the sphere is taken on one axis and the total phase difference amount $\theta_A$ is taken on the other axis. Accordingly, for example, in a case where a content of the spheres in which the minus width from the reference correlation trend line $L_S$ of the total phase difference amount $\theta_A$ is equal to or more than a first threshold value is equal to or more than a second threshold value, it can be determined that the culture lot is a bad lot, and in a case where the content of the spheres is less than the second threshold value, it can be determined that the culture lot is a good lot.

Figure 9C:
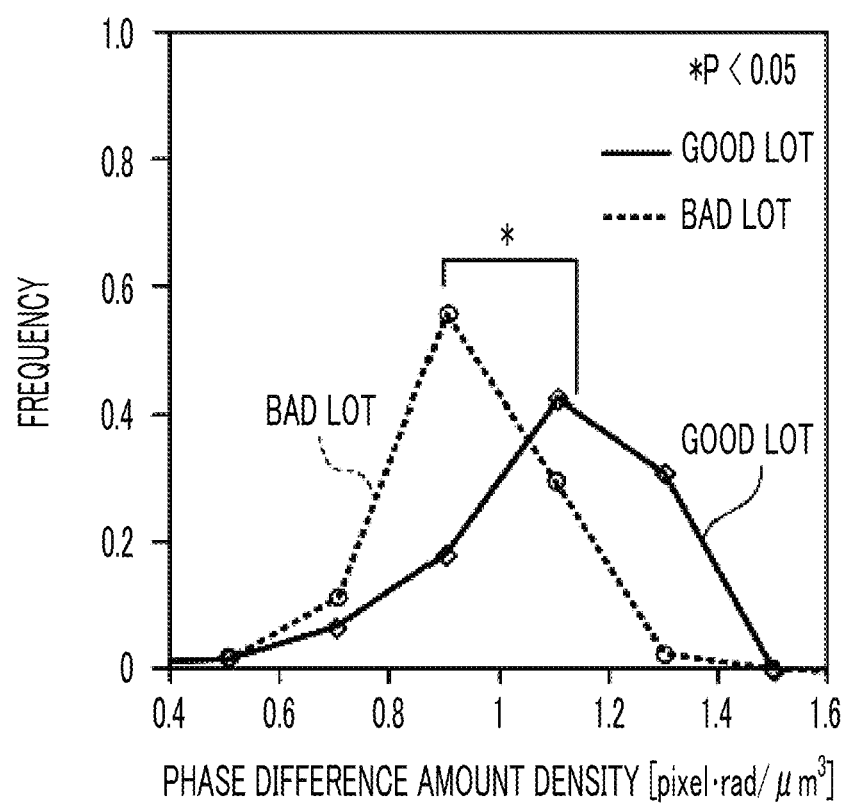
FIG. 9C is a histogram of phase difference amount densities acquired for each of a good lot and a bad lot according to an embodiment of the disclosed technology.

Next, the phase difference amount density $D_P$ shown by Formula 4 is derived from the phase difference images of each sphere obtained for each of the good lot and the bad lot. FIG. 9C is a histogram of the phase difference amount density $D_P$ acquired for each of a good lot and a bad lot. As shown in FIG. 9C, there is a significant difference in the histogram between the good lot and the bad lot. Specifically, in the good lot, a peak of distribution exists at a position where the phase difference amount density $D_P$ is relatively high, and in the bad lot, a peak of distribution exists at a position where the phase difference amount density $D_P$ is relatively low. A p value (significance probability), which is an index showing the reliability of the significant difference between the good lot and the bad lot in the histogram of the phase difference amount density $D_P$, is less than 0.05.

From the above results, it can be said that the quality of the culture lot can be determined on the basis of the phase difference amount density $D_P$ of the sphere. Therefore, for example, an average value of the phase difference amount density $D_P$ is obtained for the plurality of spheres belonging to the culture lot to be determined, and in a case where the average value is equal to or more than a threshold value, the culture lot can be determined as a good lot, and in a case where the average value is less than the threshold value, the culture lot can be determined as a bad lot.

In this example, the case where the phase difference amount density $D_P$ is used for the quality determination of the culture lot is exemplified, but the phase difference amount density $D_P$ can also be used for quality determination of a single sphere. For example, it can be determined that the state of the sphere is good in a case where the phase difference amount density $D_P$ acquired for the sphere to be determined is equal to or more than a threshold value, and it can be determined that the state of the sphere is abnormal in a case where the phase difference amount density $D_P$ is less than the threshold value.

Example 3

In this example, a plurality of spheres belonging to a plurality of different culture lots are used as an object to be determined. The spheres to be determined are all spheres of iPS cells cultured by the three-dimensional culture method.

For each of the plurality of culture lots, the sphere as the sample 14 is set on the sample stage of the imaging system 1 shown in FIG. 1, and holograms of the plurality of spheres are imaged by the CMOS camera 19. A computer numerical calculation is performed on the acquired hologram of each sphere to acquire the phase difference image sliced near the center of the sphere. For the obtained phase difference image of each sphere, the phase difference amount density $D_P$ shown by Formula 4 is derived for each culture lot.

Next, the survival rate of cells is acquired for each of the plurality of culture lots. The procedure for measuring the survival rate is as follows. A sphere accommodated in a centrifuge tube is subjected to a centrifugal separation treatment of 400 G (G: gravity acceleration) for 3 minutes. The sphere settled to the bottom of the centrifuge tube is collected and decomposed into single cells using TrypLE (registered trademark) Select, which is a cell dissociation enzyme. After the decomposed cells are subjected to a dead cell staining treatment by Trypan Blue, the number of stained dead cells is counted by counting the cells using a commercially available general cell counter (Countess (registered trademark)). The survival rate of cells is derived for each culture lot from the count of dead cells.

Figure 10:
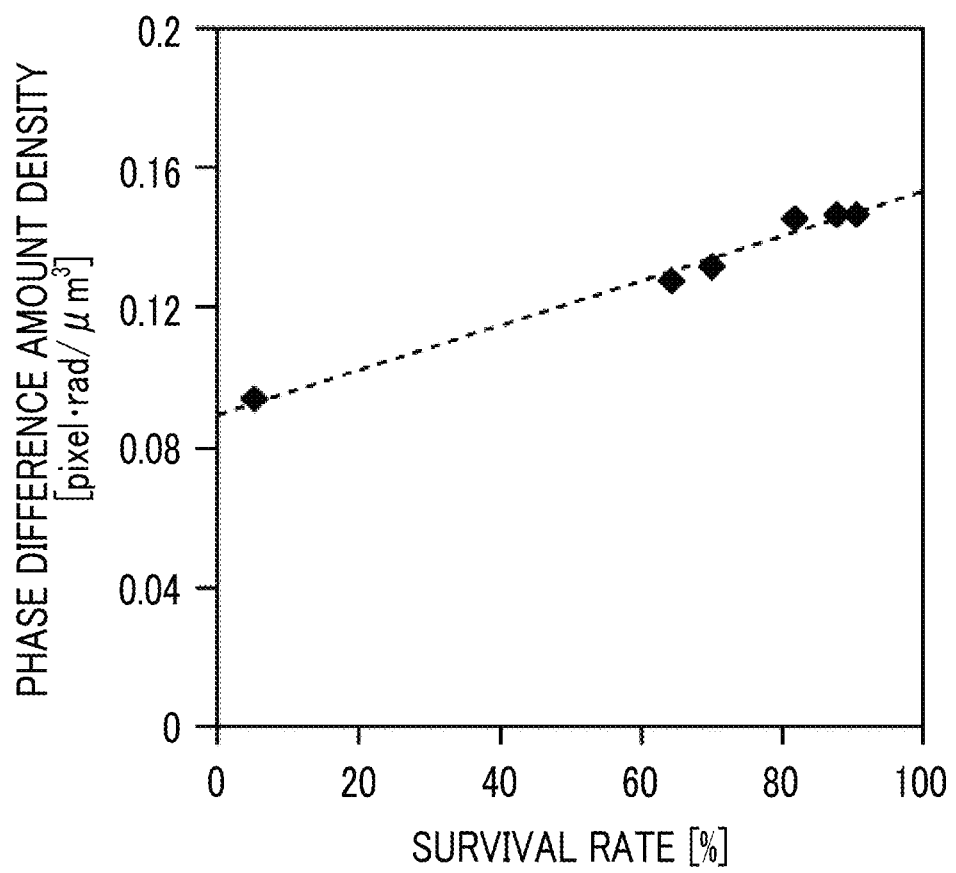
FIG. 10 is a graph showing an example of correlation properties between a survival rate of cells and a phase difference amount density according to an embodiment of the disclosed technology.

Correlation properties between the survival rate of cells and the phase difference amount density $D_P$ (lot average value) are acquired by forming a plot for each culture lot on a graph in which the survival rate of cells is taken on the lateral axis and the phase difference amount density $D_P$ is taken on the vertical axis. FIG. 10 is a graph showing the correlation properties between the survival rate of cells and the phase difference amount density $D_P$ (lot average value). As shown in FIG. 10, it is confirmed that the survival rate of cells and the phase difference amount density $D_P$ have a proportional relationship.

From the above results, it can be said that the survival rate of cells can be estimated from the phase difference amount density $D_P$. By estimating the survival rate of the cells from the phase difference amount density $D_P$, the survival rate of the cells can be grasped without performing a treatment involving destruction of the cells such as a centrifugal separation treatment and a staining treatment (that is, in a non-destructive manner). For example, a correlation line showing the correlation between the survival rate of the cells and the phase difference amount density $D_P$ is acquired in advance, and the survival rate of the cells in the culture lot can be estimated from the average value of the phase difference amount density $D_P$ acquired for the sphere belonging to the culture lot to be determined and the correlation line.

In this example, the case where the survival rate of cells in the culture lot is estimated from the phase difference amount density $D_P$ is exemplified, but it is also possible to estimate the survival rate of the cells within a single sphere from the phase difference amount density $D_P$. For example, the correlation line showing the correlation between the survival rate of the cells and the phase difference amount density $D_P$ is acquired in advance, and the survival rate of the cells in the sphere can be estimated from the phase difference amount density $D_P$ acquired for the sphere to be determined and the correlation line.

Example 4

The effect of the survival rate of cells on the phase difference image is confirmed. In order to induce necrosis in the iPS cells cultured by the two-dimensional culture method (adhesive culture method), 3 wt % of $H_2O_2$ (hydrogen peroxide) is added to a cell colony, and then staining treatment with SYTOX (registered trademark) Green as a fluorescent coloring agent is performed. Subsequently, the colony subjected to the above-described processing is set on the sample stage of the imaging system 1 shown in FIG. 1, and a hologram of the colony is imaged by the CMOS camera 19. A computer numerical calculation is performed on the acquired hologram to acquire the phase difference image of the colony. In parallel with the hologram imaging, a fluorescence microscope image is imaged by the CMOS camera 36.

Figure 11A:
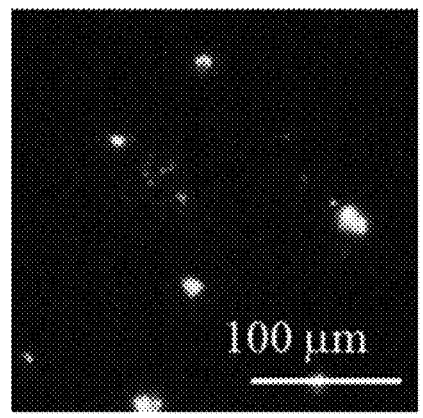
FIG. 11A is a fluorescence microscope image of a colony at a point in time where 0 minute has elapsed after $H_2O_2$ is added.
Figure 11B:
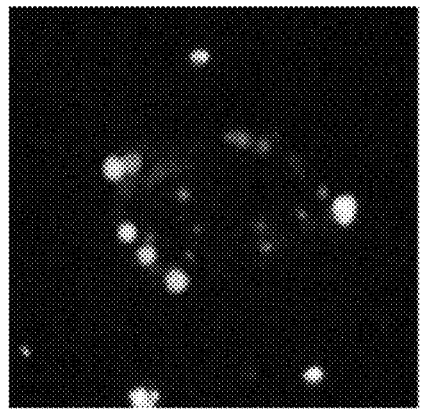
FIG. 11B is a fluorescence microscope image of a colony at a point in time where 15 minutes have elapsed after $H_2O_2$ is added.
Figure 11C:
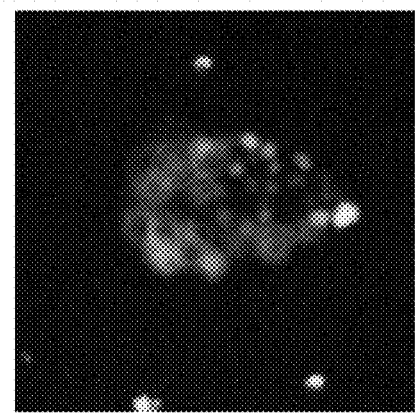
FIG. 11C is a fluorescence microscope image of a colony at a point in time where 37 minutes have elapsed after $H_2O_2$ is added.
Figure 12A:
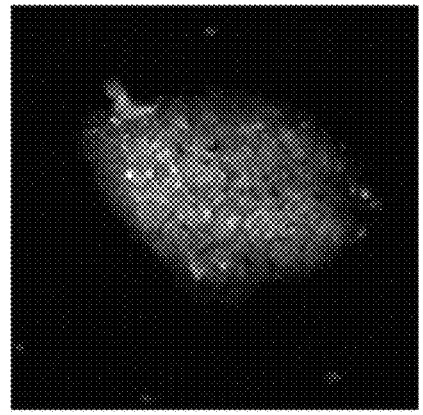
FIG. 12A is a phase difference image of a colony at a point in time where 0 minute has elapsed after $H_2O_2$ is added.
Figure 12B:
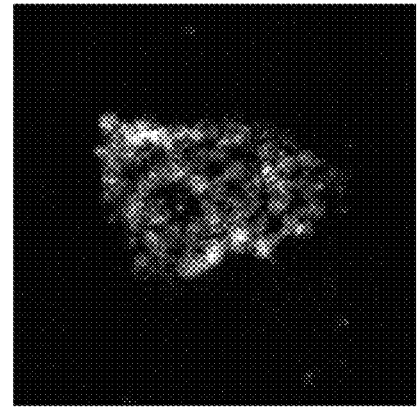
FIG. 12B is a phase difference image of a colony at a point in time where 15 minutes have elapsed after $H_2O_2$ is added.
Figure 12C:
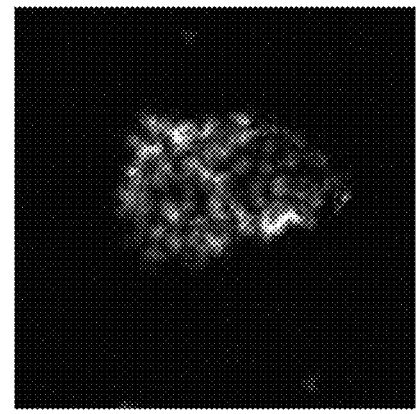
FIG. 12C is a phase difference image of a colony at a point in time where 37 minutes have elapsed after $H_2O_2$ is added.

FIGS. 11A, 11B, and 11C are fluorescence microscope images of colonies at a point in time where 0 minute, 15 minutes, and 37 minutes have elapsed after adding $H_2O_2$, respectively. FIGS. 12A, 12B, and 12C are phase difference images of colonies at a point in time where 0 minute, 15 minutes, and 37 minutes have elapsed after adding $H_2O_2$, respectively.

As shown in FIGS. 11A to 11C, the number of light emission sites increased with the lapse of time from the time at which $H_2O_2$ is added. This means that the dead cells increase (in other words, the survival rate of cells decreases) with the lapse of time from the time at which $H_2O_2$ is added. In addition, as shown in FIGS. 12A to 12C, the area of the low luminance region in the phase difference image increases with the lapse of time from the time at which $H_2O_2$ is added. This means that the total phase difference amount $\theta_A$ in the phase difference image decreases as the survival rate of cells decreases. As described above, it is confirmed that the survival rate of cells affects the total phase difference amount $\theta_A$.

Example 5

Necrosis is induced by adding $H_2O_2$ to the colonies of iPS cells cultured by the two-dimensional culture method (adhesive culture method). In addition, another iPS cell colony is induced to undergo apoptosis using Apoptosis Inducer Set from PromoKine. The apoptosis is an active cell death that is managed and regulated as a growth control mechanism in cells of multicellular organisms. On the other hand, the necrosis is passive cell death caused by external environmental factors such as nutritional deficiency, toxic substances, and trauma, and the process leading to cell death is different from apoptosis.

The colony subjected to the above-described processing and healthy colony are set on the sample stage of the imaging system 1 shown in FIG. 1, and a hologram of each colony is imaged by the CMOS camera 19. A computer numerical calculation is performed on the acquired hologram to acquire the phase difference image of each colony. For the phase difference image of each colony, the total phase difference amount $\theta_A$ shown by Formula 3 is derived.

Figure 13:
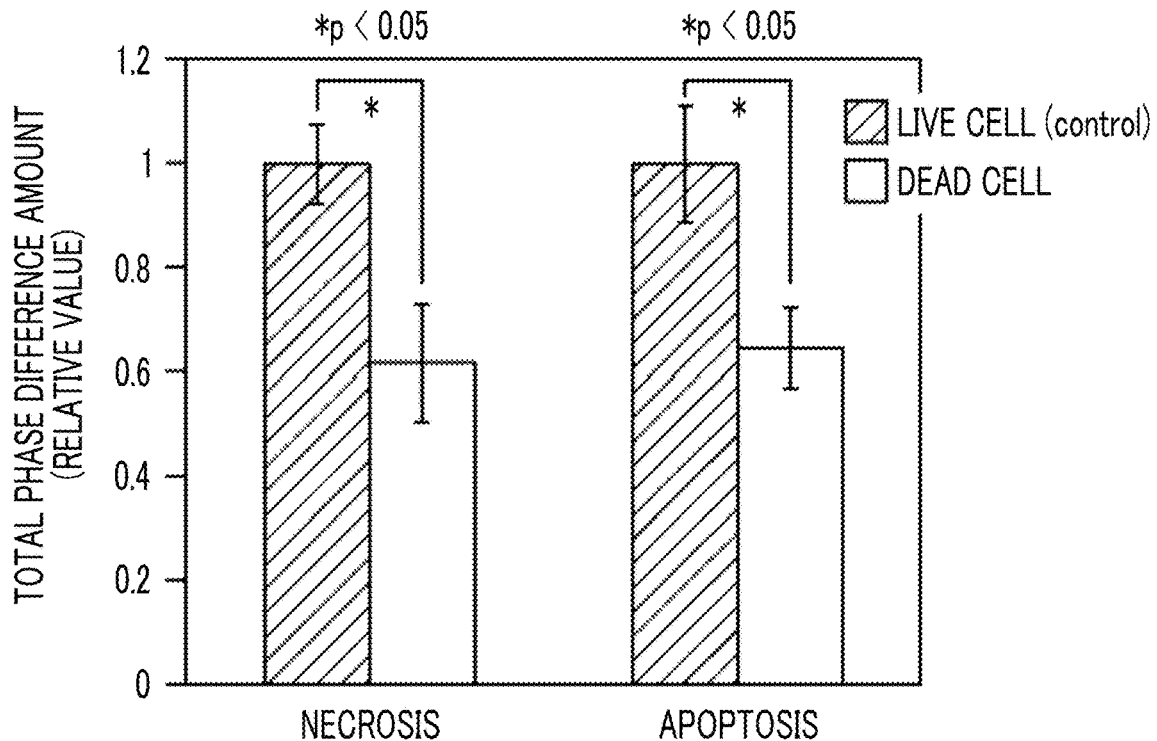
FIG. 13 is a graph showing a relative value of a total phase difference amount of each of a colony induced by necrosis, a colony induced by apoptosis, and a healthy colony according to an embodiment of the disclosed technology.

FIG. 13 is a graph showing a relative value of the total phase difference amount $\theta_A$ of each of a colony (dead cell) induced by necrosis, a colony (dead cell) induced by apoptosis, and a healthy colony (live cell). The total phase difference amount $\theta_A$ of the healthy colony (live cell) is set to 1. As shown in FIG. 13, a significant difference is observed in the total phase difference amount $\theta_A$ between the healthy colony (live cell) and the colony (dead cell) induced by necrosis and the colony (dead cell) induced by apoptosis. The p value (significance probability), which is an index showing the reliability of the significant difference, is less than 0.05.

From the above results, regardless of whether the process leading to cell death is necrosis or apoptosis, it can be said that the total phase difference amount $\theta_A$ can be used for determining whether the cells are live or dead. For example, in a case where the total phase difference amount $\theta_A$ acquired for the sphere to be determined is equal to or more than a threshold value, it can be determined that the sphere includes more live cells, and in a case where the total phase difference amount $\theta_A$ acquired for the sphere to be determined is less than the threshold value, it can be determined that the sphere includes more dead cells. It is also possible to use the phase difference amount density $D_P$ instead of the total phase difference amount $\theta_A$ to determine whether the cell is live or dead.

Example 6

A sphere of iPS cells maintained in the undifferentiated state and a sphere of iPS cells deviated from the undifferentiated state are set on the sample stage of the imaging system 1 shown in FIG. 1, and the hologram of each sphere is imaged by the CMOS camera 19. A computer numerical calculation is performed on the acquired hologram of each sphere to acquire the phase difference image sliced near the center of the sphere. For the phase difference image of each sphere, the total phase difference amount $\theta_A$ shown by Formula 3 is derived. The sphere deviated from the undifferentiated state is induced to the undifferentiated deviation state by using a basal medium to which components necessary for maintaining the undifferentiated state are not added.

Figure 14:
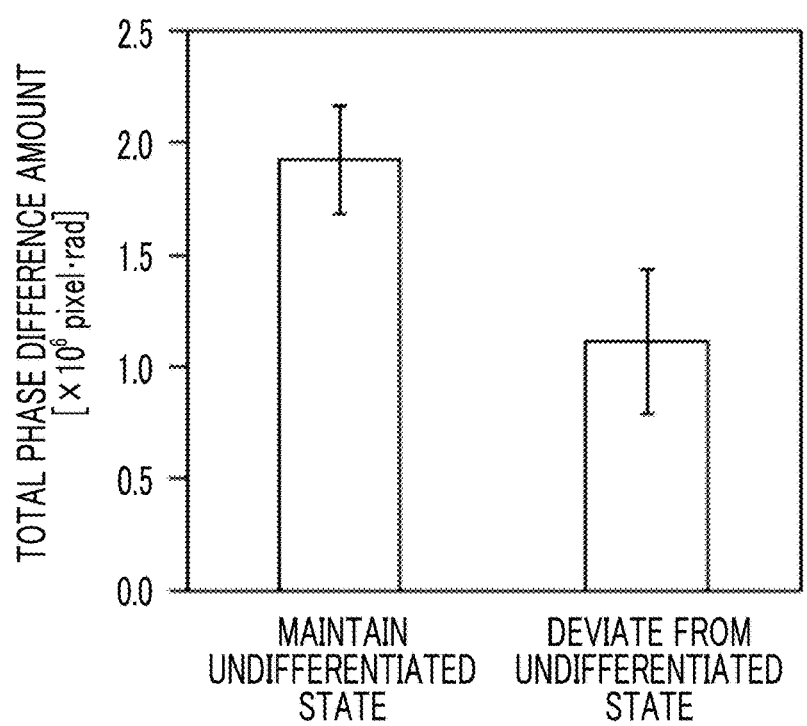
FIG. 14 is a graph showing an average value of a total phase difference amount of each of a sphere maintained in the undifferentiated state and a sphere deviated from the undifferentiated state according to the embodiment of the disclosed technology.

FIG. 14 is a graph showing an average value of the total phase difference amount $\theta_A$ of each of the spheres maintained in the undifferentiated state and the sphere deviated from the undifferentiated state. As shown in FIG. 14, a significant difference is found in the total phase difference amount $\theta_A$ between the sphere that maintained the undifferentiated state and the sphere that deviated from the undifferentiated state.

From the above results, it can be said that the total phase difference amount $\theta_A$ can be used for determining whether an undifferentiated state of a stem cell is maintained or deviated from the undifferentiated state. For example, in the case where the total phase difference amount $\theta_A$ acquired for the sphere to be determined is equal to or more than a threshold value, it can be determined that the sphere maintains the undifferentiated state, and in the case where the total phase difference amount $\theta_A$ acquired for the sphere to be determined is less than the threshold value, it can be determined that the sphere deviates from the undifferentiated state. It is also possible to use the phase difference amount density $D_P$ instead of the total phase difference amount $\theta_A$ for determining whether the undifferentiated state is maintained or deviated.

As is clear from the above description, according to the determination method of the embodiment of the disclosed technology, the state of the sphere is determined on the basis of the phase difference image generated from the hologram of the sphere and the shape index value corresponding to the shape of the sphere, and thus the state of the sphere can be determined in a non-destructive and simple manner.

That is, according to the determination method of the embodiment of the disclosed technology, it is possible to determine the density, the survival rate, or the like of cells inside the sphere that cannot be grasped by the conventional optical microscope. In addition, imaging of hologram, an image analysis, statistical processing, and the like performed in this determination method can be easily automated by a computer, and labor and processing time can be reduced as compared with conventional methods. Further, it is possible to obtain a stable determination result without affecting the variation of techniques by operators. Further, it is possible to determine the state of the sphere non-destructively without performing a treatment involving cell destruction such as decomposing the sphere into single cells or adding a fluorescent coloring agent. Additionally, the hologram imaging can be easily performed even for spheres randomly present in a three-dimensional space, and the state of the sphere during culture by the three-dimensional culture method can be determined on the spot.

In the determination of the state of the sphere, a more accurate determination result can be obtained by using the phase difference image sliced near the center of the spherical sphere. By using one phase difference image sliced near the center of the spherical sphere, it is possible to simplify the processing required for determination, as compared with the case of using a plurality of phase difference images having different slice positions.

A determination method according to the disclosed technology includes generating a phase difference image of a sphere that is an aggregate of a plurality of cells from a hologram obtained by imaging the sphere; and determining a state of the sphere on the basis of the phase difference image and a shape index value corresponding to a shape of the sphere.

In the determination method according to the disclosed technology, it is possible to determine the state of the sphere in a non-destructive and simple manner.

In the determination method according to the disclosed technology, a determination regarding at least one of a survival rate, a density, a homogeneity, or an undifferentiated state deviation of the plurality of cells included in the sphere, or an outer shape of the sphere may be performed on the basis of the phase difference image and the shape index value.

In the determination method according to the disclosed technology, a total phase difference amount that is a value obtained by integrating a phase difference amount of each of a plurality of pixels constituting the phase difference image may be derived; and the state of the sphere may be determined using a correlation between the total phase difference amount and the shape index value.

By using the correlation between the total phase difference amount and the shape index value to determine the state of the sphere, it is possible to make an accurate determination of the state of the sphere.

In the determination method according to the disclosed technology, a reference correlation trend line indicating a reference for the correlation between the total phase difference amount and the shape index value may be compared with a correlation between a total phase difference amount and a shape index value for a sphere to be determined; and the state of the sphere to be determined may be determined according to a degree of deviation of the correlation between the total phase difference amount and the shape index value for the sphere to be determined from the reference correlation trend line. For example, in a case where a width of the deviation of the correlation between the total phase difference amount and the shape index value for the sphere to be determined from the reference correlation trend line exceeds a threshold value, it may be determined that there is an abnormality in at least one of a survival rate, a density, or a homogeneity of cells included in the sphere to be determined, or an outer shape of the sphere.

According to this aspect, it is possible to further improve the accuracy of the state determination of the sphere.

In the determination method according to the disclosed technology, a reference correlation trend line indicating a reference for the correlation between the total phase difference amount and the shape index value may be compared with a correlation between a total phase difference amount and a shape index value for each of a plurality of spheres belonging to a culture lot to be determined; and a quality of the culture lot to be determined may be determined according to at least one of a state of deviation or a degree of deviation of the correlation between the total phase difference amount and the shape index value for the culture lot to be determined from the reference correlation trend line.

According to this aspect, it becomes possible to accurately determine the quality of the culture lot including a plurality of spheres.

In the determination method according to the disclosed technology, the shape index value may be any one of a volume, a cross-sectional area, a particle diameter, or a circumferential length of the sphere.

In the determination method according to the disclosed technology, a phase difference amount density may be derived by dividing a total phase difference amount that is a value obtained by integrating a phase difference amount of each of a plurality of pixels constituting the phase difference image by a volume of the sphere; and the state of the sphere may be determined on the basis of the phase difference amount density.

By using the phase difference amount density to determine the state of the sphere, it is possible to make an accurate determination of the state of the sphere.

In the determination method according to the disclosed technology, it is preferable that the phase difference image used for the determination of the state of the sphere is a phase difference image in which variation in a phase difference amount between a plurality of pixels constituting the phase difference image is the maximum among a plurality of phase difference images that can be generated from the hologram.

By using the above-described image as the phase difference image used to determine the state of the sphere, more accurate information matching the actual condition of the sphere can be obtained from the phase difference image, and the accuracy of the state determination of the sphere can be further improved.

EXPLANATION OF REFERENCES

1: imaging system
10: hologram optical system
11: laser light source
12: beam splitter
13: collimating lens
14: sample
15: objective lens
17: imaging lens
18: beam splitter
19, 36: CMOS camera
20: optical fiber
21: collimating lens
30: fluorescence microscope optical system
31: excitation light source
32: excitation filter
33: ON/OFF switching mirror
34: dichroic mirror
35: spectral filter 500: computer
502: main memory
503: auxiliary storage device
504: communication interface
505: display unit
506: autofocus program
507: bus
$D_P$: phase difference amount density
$I_P$: phase difference image
$L_s$: reference correlation trend line
θ: phase difference amount
$θ_B$: phase of background
$θ_S$: phase of region where sphere exist
$θ_A$: total phase difference amount
$θ_k$: phase difference amount $θ_k$ per 1 pixel
V: volume of sphere
$v_k$: volume of sphere in portion corresponding to each pixel k of phase difference image
a1, a2, a3, a4, a5: plot
k: pixel
w: width of curve

What is claimed is:

1. A determination method, comprising:
generating a phase difference image of a sphere that is an aggregate of a plurality of cells from a hologram obtained by imaging the sphere, wherein the phase difference image is a phase difference image of the sphere at a slice position in which variation in a phase difference amount between a plurality of pixels constituting the phase difference image is the maximum among a plurality of phase difference images that are generable from the hologram; and
determining a state of the sphere on the basis of the phase difference image and a shape index value corresponding to a shape of the sphere.

2. The determination method according to claim 1, further comprising:
performing determination regarding at least one of a survival rate, a density, a homogeneity, or an undifferentiated state deviation of the plurality of cells included in the sphere, or an outer shape of the sphere, on the basis of the phase difference image and the shape index value.

3. The determination method according to claim 2, further comprising:
deriving a total phase difference amount that is a value obtained by integrating a phase difference amount of each of the plurality of pixels constituting the phase difference image; and
determining the state of the sphere using a correlation between the total phase difference amount and the shape index value.

4. The determination method according to claim 2,
wherein the shape index value is any one of a volume, a cross-sectional area, a particle diameter, or a circumferential length of the sphere.

5. The determination method according to claim 3, further comprising:
comparing a reference correlation trend line indicating a reference for the correlation between the total phase difference amount and the shape index value with a correlation between a total phase difference amount and a shape index value for a sphere to be determined; and
determining the state of the sphere to be determined according to a degree of deviation of the correlation between the total phase difference amount and the shape index value for the sphere to be determined from the reference correlation trend line.

6. The determination method according to claim 3, further comprising:
comparing a reference correlation trend line indicating a reference for the correlation between the total phase difference amount and the shape index value with a correlation between a total phase difference amount and a shape index value for each of a plurality of spheres belonging to a culture lot to be determined; and
determining a quality of the culture lot to be determined according to at least one of a state of deviation or a degree of deviation of the correlation between the total phase difference amount and the shape index value for the culture lot to be determined from the reference correlation trend line.

7. The determination method according to claim 3,
wherein the shape index value is any one of a volume, a cross-sectional area, a particle diameter, or a circumferential length of the sphere.

8. The determination method according to claim 5, further comprising:
determining that there is an abnormality in at least one of a survival rate, a density, or a homogeneity of cells included in the sphere to be determined, or an outer shape of the sphere in a case where a width of the deviation of the correlation between the total phase difference amount and the shape index value for the sphere to be determined from the reference correlation trend line exceeds a threshold value.

9. The determination method according to claim 5,
wherein the shape index value is any one of a volume, a cross-sectional area, a particle diameter, or a circumferential length of the sphere.

10. The determination method according to claim 8,
wherein the shape index value is any one of a volume, a cross-sectional area, a particle diameter, or a circumferential length of the sphere.

11. The determination method according to claim 1, further comprising:
deriving a total phase difference amount that is a value obtained by integrating a phase difference amount of each of the plurality of pixels constituting the phase difference image; and
determining the state of the sphere using a correlation between the total phase difference amount and the shape index value.

12. The determination method according to claim 11, further comprising:
comparing a reference correlation trend line indicating a reference for the correlation between the total phase difference amount and the shape index value with a correlation between a total phase difference amount and a shape index value for a sphere to be determined; and
determining the state of the sphere to be determined according to a degree of deviation of the correlation between the total phase difference amount and the shape index value for the sphere to be determined from the reference correlation trend line.

13. The determination method according to claim 12, further comprising:
determining that there is an abnormality in at least one of a survival rate, a density, or a homogeneity of cells included in the sphere to be determined, or an outer shape of the sphere in a case where a width of the deviation of the correlation between the total phase difference amount and the shape index value for the sphere to be determined from the reference correlation trend line exceeds a threshold value.

14. The determination method according to claim 13, wherein the shape index value is any one of a volume, a cross-sectional area, a particle diameter, or a circumferential length of the sphere.

15. The determination method according to claim 12, wherein the shape index value is any one of a volume, a cross-sectional area, a particle diameter, or a circumferential length of the sphere.

16. The determination method according to claim 11, further comprising:
comparing a reference correlation trend line indicating a reference for the correlation between the total phase difference amount and the shape index value with a correlation between a total phase difference amount and a shape index value for each of a plurality of spheres belonging to a culture lot to be determined; and
determining a quality of the culture lot to be determined according to at least one of a state of deviation or a degree of deviation of the correlation between the total phase difference amount and the shape index value for the culture lot to be determined from the reference correlation trend line.

17. The determination method according to claim 11, wherein the shape index value is any one of a volume, a cross-sectional area, a particle diameter, or a circumferential length of the sphere.

18. The determination method according to claim 1, wherein the shape index value is any one of a volume, a cross-sectional area, a particle diameter, or a circumferential length of the sphere.

19. The determination method according to claim 1, further comprising:
deriving a phase difference amount density by dividing a total phase difference amount by a volume of the sphere, the total phase difference amount is a value obtained by integrating a phase difference amount of each of the plurality of pixels constituting the phase difference image; and
determining the state of the sphere on the basis of the phase difference amount density.

* * * * *